(12) United States Patent
Wu et al.

(10) Patent No.: US 7,754,197 B2
(45) Date of Patent: Jul. 13, 2010

(54) METHOD FOR REDUCING ODOR USING COORDINATED POLYDENTATE COMPOUNDS

(75) Inventors: Bin Wu, Foxboro, MA (US); Kevin P. McGrath, Alpharetta, GA (US); Jaeho Kim, Roswell, GA (US); Bao Trong Kim, Decatur, GA (US); Sharon Linda Greene, Canton, GA (US); Yanbin Huang, Roswell, GA (US); Kaiyuan Yang, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 256 days.

(21) Appl. No.: 10/686,937

(22) Filed: Oct. 16, 2003

(65) Prior Publication Data

US 2005/0084474 A1  Apr. 21, 2005

(51) Int. Cl.
*B01D 53/34* (2006.01)
*A01N 59/00* (2006.01)
*A01N 59/16* (2006.01)
*A01N 59/20* (2006.01)
*A61K 33/00* (2006.01)
*A61K 33/38* (2006.01)
*A61K 33/34* (2006.01)
*A61K 33/32* (2006.01)
*A61K 33/26* (2006.01)
*A61K 33/24* (2006.01)

(52) U.S. Cl. ............... 424/76.2; 424/600; 424/617; 424/618; 424/630; 424/639; 424/641; 424/646; 424/649

(58) Field of Classification Search ........... 424/618, 424/630, 639, 641, 646, 649, 76.1; 514/494, 514/495, 499, 501, 502, 836
See application file for complete search history.

(56) References Cited

U.S. PATENT DOCUMENTS

| | | | |
|---|---|---|---|
| 2,015,864 A | 10/1935 | Müller et al. | |
| 2,593,146 A | 4/1952 | Howard | |
| 3,266,973 A | 8/1966 | Crowley | |
| 3,338,992 A | 8/1967 | Kinney | |
| 3,341,394 A | 9/1967 | Kinney | |
| 3,381,688 A | 5/1968 | Satas | |
| 3,494,821 A | 2/1970 | Evans | |
| 3,502,538 A | 3/1970 | Petersen | |
| 3,502,763 A | 3/1970 | Hartmann | |
| 3,507,269 A | 4/1970 | Berry | |
| 3,542,615 A | 11/1970 | Dobo et al. | |
| 3,615,478 A | 10/1971 | Hoshino et al. | |
| 3,692,618 A | 9/1972 | Dorschner et al. | |
| 3,794,497 A | 2/1974 | Pratt et al. | |
| 3,802,817 A | 4/1974 | Matsuki et al. | |
| 3,836,633 A | 9/1974 | Beschke | |
| 3,849,241 A | 11/1974 | Butin et al. | |
| 3,919,437 A | 11/1975 | Brown et al. | |
| 3,960,494 A | 6/1976 | Verma et al. | |
| 3,971,665 A | 7/1976 | Suzuki et al. | |
| 4,006,030 A | 2/1977 | Yoshida et al. | |
| 4,041,203 A | 8/1977 | Brock et al. | |
| 4,078,029 A | 3/1978 | Yoshida et al. | |
| 4,100,324 A | 7/1978 | Anderson et al. | |
| 4,101,638 A | 7/1978 | Inoue et al. | |
| 4,144,370 A | 3/1979 | Boulton | |
| 4,172,781 A | 10/1979 | Walk et al. | |
| 4,275,054 A * | 6/1981 | Sebag et al. ............ 424/65 |
| 4,297,233 A | 10/1981 | Gualandi | |
| RE30,797 E | 11/1981 | Davis | |
| RE30,803 E | 11/1981 | Davis | |
| 4,313,820 A | 2/1982 | Farha, Jr. et al. | |
| 4,340,563 A | 7/1982 | Appel et al. | |
| 4,375,448 A | 3/1983 | Appel et al. | |
| 4,407,960 A | 10/1983 | Tratnyek | |
| 4,467,012 A | 8/1984 | Pedersen et al. | |
| 4,469,746 A | 9/1984 | Weisman et al. | |
| 4,488,969 A | 12/1984 | Hou | |
| 4,494,278 A | 1/1985 | Kroyer et al. | |
| 4,494,629 A | 1/1985 | Raeburn | |
| 4,517,308 A | 5/1985 | Ehlenz et al. | |
| 4,522,203 A | 6/1985 | Mays | |
| 4,525,410 A | 6/1985 | Hagiwara et al. | |
| 4,575,556 A | 3/1986 | Byrne et al. | |
| 4,604,313 A | 8/1986 | McFarland et al. | |
| 4,640,810 A | 2/1987 | Laursen et al. | |

(Continued)

FOREIGN PATENT DOCUMENTS

EP    0103214 B1    3/1984

(Continued)

OTHER PUBLICATIONS

Derwent-ACC-No. 1992-393132; Abstracting JP 04290547.*

(Continued)

*Primary Examiner*—Ernst V Arnold
(74) *Attorney, Agent, or Firm*—Dority & Manning, P.A.

(57) ABSTRACT

A method for reducing odor is provided. The method comprises forming a coordination complex between a transition metal and a polydentate compound, and contacting the coordinated complex with an odorous compound. The transition metal provides one or more active sites for capturing the odorous compound. In some embodiments, the polydentate compound may be a polyalkylimine, such as polyethyleneimine, polypropyleneimine, or a dendrimer thereof.

26 Claims, No Drawings

U.S. PATENT DOCUMENTS

| | | |
|---|---|---|
| 4,643,801 A | 2/1987 | Johnson |
| 4,655,757 A | 4/1987 | McFarland et al. |
| 4,701,218 A | 10/1987 | Barker et al. |
| 4,715,983 A | 12/1987 | Ota et al. |
| 4,725,415 A | 2/1988 | Kidd |
| 4,734,324 A | 3/1988 | Hill |
| RE32,649 E | 4/1988 | Brandt et al. |
| 4,775,585 A | 10/1988 | Hagiwara |
| 4,780,448 A | 10/1988 | Broecker et al. |
| 4,781,858 A | 11/1988 | Mizukami et al. |
| 4,783,220 A | 11/1988 | Gamble et al. |
| 4,798,603 A | 1/1989 | Meyer et al. |
| 4,802,473 A | 2/1989 | Hubbard et al. |
| 4,818,464 A | 4/1989 | Lau |
| 4,823,404 A | 4/1989 | Morell et al. |
| 4,823,803 A | 4/1989 | Nakamura |
| 4,904,304 A | 2/1990 | Watanabe et al. |
| 4,959,135 A * | 9/1990 | Zenner et al. ............... 205/633 |
| 4,969,457 A | 11/1990 | Hubbard et al. |
| 4,978,615 A | 12/1990 | Aoyama et al. |
| 4,988,505 A | 1/1991 | Watanabe et al. |
| 5,000,746 A | 3/1991 | Meiss |
| 5,003,178 A | 3/1991 | Livesay |
| 5,020,533 A | 6/1991 | Hubbard et al. |
| 5,057,302 A | 10/1991 | Johnson et al. |
| 5,064,473 A | 11/1991 | Kubo et al. |
| 5,100,581 A | 3/1992 | Watanabe et al. |
| 5,100,702 A | 3/1992 | Maeda et al. |
| 5,102,597 A | 4/1992 | Roe et al. |
| 5,108,739 A | 4/1992 | Kurihara et al. |
| 5,120,693 A * | 6/1992 | Connolly et al. ............... 502/64 |
| 5,122,418 A | 6/1992 | Nakane et al. |
| 5,133,803 A | 7/1992 | Moffatt |
| 5,145,518 A | 9/1992 | Winnik et al. |
| 5,145,727 A | 9/1992 | Potts et al. |
| 5,169,706 A | 12/1992 | Collier, IV et al. |
| 5,178,931 A | 1/1993 | Perkins et al. |
| 5,183,656 A | 2/1993 | Uesaka et al. |
| 5,188,885 A | 2/1993 | Timmons et al. |
| 5,196,177 A | 3/1993 | Watanabe et al. |
| 5,204,429 A | 4/1993 | Kaminsky et al. |
| 5,209,998 A | 5/1993 | Kavassalis et al. |
| 5,220,000 A | 6/1993 | Theodoropulos |
| 5,221,497 A | 6/1993 | Watanabe et al. |
| 5,225,374 A | 7/1993 | Fare et al. |
| 5,230,953 A | 7/1993 | Tsugeno et al. |
| 5,238,518 A | 8/1993 | Okubi et al. |
| 5,245,117 A | 9/1993 | Withers et al. |
| 5,266,289 A | 11/1993 | Tsugeno et al. |
| 5,284,703 A | 2/1994 | Everhart et al. |
| 5,292,868 A | 3/1994 | Subramanian |
| 5,294,717 A | 3/1994 | Theodoropulos |
| 5,300,365 A | 4/1994 | Ogale |
| 5,308,641 A | 5/1994 | Cahalan et al. |
| 5,322,061 A | 6/1994 | Brunson |
| 5,332,432 A | 7/1994 | Okubi et al. |
| 5,338,713 A | 8/1994 | Takagi et al. |
| 5,342,876 A | 8/1994 | Abe et al. |
| 5,350,624 A | 9/1994 | Georger et al. |
| 5,366,947 A | 11/1994 | Muller et al. |
| 5,382,400 A | 1/1995 | Pike et al. |
| 5,383,450 A | 1/1995 | Hubbard et al. |
| 5,397,667 A | 3/1995 | Law et al. |
| 5,407,442 A | 4/1995 | Karapasha |
| 5,407,600 A | 4/1995 | Ando et al. |
| 5,420,090 A | 5/1995 | Spencer et al. |
| 5,427,844 A | 6/1995 | Murai et al. |
| 5,429,628 A | 7/1995 | Trinh et al. |
| 5,432,000 A | 7/1995 | Young, Sr. et al. |
| 5,451,450 A | 9/1995 | Erderly et al. |
| 5,458,864 A | 10/1995 | Tsugeno et al. |
| 5,472,775 A | 12/1995 | Obijeski et al. |
| 5,480,636 A | 1/1996 | Maruo et al. |
| 5,486,356 A | 1/1996 | Yim |
| 5,487,938 A | 1/1996 | Spencer et al. |
| 5,488,126 A | 1/1996 | Subramanian et al. |
| 5,527,171 A | 6/1996 | Soerensen |
| 5,536,254 A | 7/1996 | McVay |
| 5,538,548 A | 7/1996 | Yamazaki |
| 5,539,124 A | 7/1996 | Etherton et al. |
| 5,540,916 A | 7/1996 | Parks |
| 5,547,607 A | 8/1996 | Ando et al. |
| 5,553,608 A | 9/1996 | Reese et al. |
| 5,554,775 A | 9/1996 | Krishnamurti et al. |
| 5,580,655 A | 12/1996 | El-Shall et al. |
| 5,583,219 A | 12/1996 | Subramanian et al. |
| 5,591,797 A | 1/1997 | Barthel et al. |
| 5,597,512 A | 1/1997 | Watanabe et al. |
| 5,661,198 A | 8/1997 | Inatani et al. |
| 5,663,224 A | 9/1997 | Emmons et al. |
| 5,679,138 A | 10/1997 | Bishop et al. |
| 5,679,724 A | 10/1997 | Sacripante et al. |
| 5,695,868 A | 12/1997 | McCormack |
| 5,733,272 A | 3/1998 | Brunner et al. |
| 5,747,003 A | 5/1998 | Mohnot et al. |
| 5,773,227 A | 6/1998 | Kuhn et al. |
| 5,795,985 A | 8/1998 | Husler et al. |
| 5,807,636 A | 9/1998 | Sheu et al. |
| 5,813,398 A | 9/1998 | Baird et al. |
| 5,817,300 A | 10/1998 | Cook et al. |
| 5,837,352 A | 11/1998 | English et al. |
| 5,843,509 A | 12/1998 | Calvo Salve et al. |
| 5,855,788 A | 1/1999 | Everhart et al. |
| 5,861,144 A | 1/1999 | Peterson et al. |
| 5,871,872 A | 2/1999 | Matijevic et al. |
| 5,874,067 A | 2/1999 | Lucas et al. |
| 5,880,176 A | 3/1999 | Kamoto et al. |
| 5,880,309 A | 3/1999 | Suzuki et al. |
| 5,882,638 A | 3/1999 | Dodd et al. |
| 5,885,599 A | 3/1999 | Peterson et al. |
| 5,897,541 A | 4/1999 | Uitenbroek et al. |
| 5,902,226 A | 5/1999 | Tasaki et al. |
| 5,905,101 A | 5/1999 | Fujiki et al. |
| 5,916,596 A | 6/1999 | Desai et al. |
| 5,948,398 A | 9/1999 | Hanamoto et al. |
| 5,948,483 A | 9/1999 | Kim et al. |
| 5,962,566 A | 10/1999 | Grandfils et al. |
| 5,962,995 A | 10/1999 | Avnery |
| 5,964,926 A | 10/1999 | Cohen |
| 5,972,389 A | 10/1999 | Shell et al. |
| 5,985,229 A | 11/1999 | Yamada et al. |
| 5,989,510 A | 11/1999 | Abe et al. |
| 5,989,515 A | 11/1999 | Watanabe et al. |
| 6,001,342 A * | 12/1999 | Forestier et al. ............ 424/76.1 |
| 6,004,625 A | 12/1999 | Oshima |
| 6,007,592 A | 12/1999 | Kasai et al. |
| 6,024,786 A | 2/2000 | Gore |
| 6,045,900 A | 4/2000 | Haffner et al. |
| 6,047,413 A | 4/2000 | Welchel et al. |
| 6,060,410 A | 5/2000 | Gillberg-LaForce et al. |
| 6,073,771 A | 6/2000 | Pressley et al. |
| 6,075,179 A | 6/2000 | McCormack et al. |
| 6,096,299 A | 8/2000 | Guarracino et al. |
| 6,111,163 A | 8/2000 | McCormack et al. |
| 6,172,173 B1 | 1/2001 | Spencer et al. |
| 6,177,608 B1 | 1/2001 | Weinstrauch |
| 6,190,814 B1 | 2/2001 | Law et al. |
| 6,193,844 B1 | 2/2001 | McLaughlin et al. |
| 6,225,524 B1 | 5/2001 | Guarracino et al. |
| 6,238,767 B1 | 5/2001 | McCormack et al. |
| 6,254,894 B1 | 7/2001 | Denkewicz, Jr. et al. |
| 6,264,615 B1 | 7/2001 | Diamond et al. |
| 6,277,346 B1 | 8/2001 | Murasawa et al. |
| 6,277,772 B1 | 8/2001 | Gancet et al. |

| | | |
|---|---|---|
| 6,291,535 B1 | 9/2001 | Watanabe et al. |
| 6,294,222 B1 | 9/2001 | Cohen et al. |
| 6,299,867 B1 | 10/2001 | Aoyagi et al. |
| 6,309,736 B1 | 10/2001 | McCormack et al. |
| 6,315,864 B2 | 11/2001 | Anderson et al. |
| 6,334,988 B1 | 1/2002 | Gallis et al. |
| 6,339,714 B1 | 1/2002 | Chen |
| 6,344,218 B1 | 2/2002 | Dodd et al. |
| 6,344,272 B1 | 2/2002 | Oldenburg et al. |
| 6,358,537 B1 | 3/2002 | Hoshino et al. |
| 6,358,909 B1 | 3/2002 | Ochomogo et al. |
| 6,369,290 B1 | 4/2002 | Glaug et al. |
| 6,376,741 B1 | 4/2002 | Guarracino et al. |
| 6,387,495 B1 | 5/2002 | Reeves et al. |
| 6,398,827 B1 | 6/2002 | Ota et al. |
| 6,407,492 B1 | 6/2002 | Avnery et al. |
| 6,410,616 B1 | 6/2002 | Harada et al. |
| 6,410,765 B1 | 6/2002 | Wellinhoff et al. |
| 6,425,530 B1 | 7/2002 | Coakley |
| 6,427,693 B1 | 8/2002 | Blackstock et al. |
| 6,428,814 B1 | 8/2002 | Bosch et al. |
| 6,433,243 B1 | 8/2002 | Woltman et al. |
| 6,440,187 B1 | 8/2002 | Kasai et al. |
| 6,460,989 B1 | 10/2002 | Yano et al. |
| 6,461,735 B1 | 10/2002 | Furuya et al. |
| 6,467,897 B1 | 10/2002 | Wu et al. |
| 6,468,500 B1 | 10/2002 | Sakaguchi et al. |
| 6,475,601 B1 | 11/2002 | Sakaki et al. |
| 6,479,150 B1 | 11/2002 | Liu et al. |
| 6,491,790 B1 | 12/2002 | Proverb et al. |
| 6,498,000 B2 | 12/2002 | Murasawa et al. |
| 6,517,199 B1 | 2/2003 | Tomioka et al. |
| 6,531,704 B2 | 3/2003 | Yadav et al. |
| 6,536,890 B1 | 3/2003 | Kato et al. |
| 6,548,264 B1 | 4/2003 | Tan et al. |
| 6,551,457 B2 | 4/2003 | Westman et al. |
| 6,562,441 B1 | 5/2003 | Maeda et al. |
| 6,575,383 B2 | 6/2003 | Dobler et al. |
| 6,578,521 B2 | 6/2003 | Raymond et al. |
| 6,589,562 B1 | 7/2003 | Shefer et al. |
| 6,607,711 B2 | 8/2003 | Pedersen |
| 6,623,848 B2 | 9/2003 | Brehm et al. |
| 6,638,918 B2 | 10/2003 | Davison et al. |
| 6,639,004 B2 | 10/2003 | Falat et al. |
| 6,645,569 B2 | 11/2003 | Cramer et al. |
| 6,693,071 B2 | 2/2004 | Ghosh et al. |
| 2001/0000889 A1 | 5/2001 | Yadav et al. |
| 2001/0023338 A1 | 9/2001 | Guarracino et al. |
| 2001/0031248 A1 | 10/2001 | Hall-Puzio et al. |
| 2001/0056246 A1 | 12/2001 | Rodriguez-Fernandez |
| 2002/0005145 A1 | 1/2002 | Sherman |
| 2002/0066542 A1 | 6/2002 | Jakob et al. |
| 2002/0091071 A1 | 7/2002 | Fischer et al. |
| 2002/0106466 A1 | 8/2002 | Hausmann et al. |
| 2002/0110686 A1 | 8/2002 | Dugan |
| 2002/0128336 A1 | 9/2002 | Kolb et al. |
| 2002/0142937 A1 | 10/2002 | Carter et al. |
| 2002/0149656 A1 | 10/2002 | Nohr et al. |
| 2002/0150678 A1 | 10/2002 | Cramer et al. |
| 2002/0176982 A1 | 11/2002 | Rohrbaugh et al. |
| 2002/0177621 A1 | 11/2002 | Hanada |
| 2002/0182102 A1 | 12/2002 | Fontenot et al. |
| 2003/0013369 A1 | 1/2003 | Soane et al. |
| 2003/0021983 A1 | 1/2003 | Nohr et al. |
| 2003/0050211 A1 | 3/2003 | Hage et al. |
| 2003/0056648 A1 | 3/2003 | Fornai et al. |
| 2003/0070782 A1 | 4/2003 | Proverb et al. |
| 2003/0082237 A1 | 5/2003 | Cha et al. |
| 2003/0100842 A1 | 5/2003 | Rosenberg et al. |
| 2003/0147956 A1 | 8/2003 | Shefer et al. |
| 2003/0147966 A1 | 8/2003 | Franzen et al. |
| 2003/0181540 A1 | 9/2003 | Quellet et al. |
| 2003/0203009 A1 | 10/2003 | MacDonald |
| 2003/0235605 A1 | 12/2003 | Lelah et al. |
| 2004/0033269 A1 | 2/2004 | Hei et al. |
| 2004/0034157 A1 | 2/2004 | Ghosh et al. |
| 2004/0043688 A1 | 3/2004 | Soerens et al. |

FOREIGN PATENT DOCUMENTS

| | | |
|---|---|---|
| EP | 0232141 A1 | 8/1987 |
| EP | 0251783 B1 | 1/1988 |
| EP | 0282287 B2 | 9/1988 |
| EP | 0339461 B1 | 11/1989 |
| EP | 0348978 A2 | 1/1990 |
| EP | 0376448 B1 | 7/1990 |
| EP | 0389015 A2 | 9/1990 |
| EP | 0389015 A3 | 9/1990 |
| EP | 0389023 A2 | 9/1990 |
| EP | 0389023 A3 | 9/1990 |
| EP | 0483500 A1 | 5/1992 |
| EP | 0510619 A1 | 10/1992 |
| EP | 0749295 B1 | 12/1996 |
| EP | 0972653 A1 | 1/2000 |
| EP | 1034800 A1 | 9/2000 |
| EP | 1157672 A1 | 11/2001 |
| EP | 1162172 A1 | 12/2001 |
| EP | 1188854 A1 | 3/2002 |
| EP | 1214878 A1 | 6/2002 |
| EP | 1216675 A1 | 6/2002 |
| EP | 1298071 A1 | 4/2003 |
| EP | 1315526 B1 | 6/2003 |
| EP | 1053788 B1 | 10/2003 |
| JP | 62149322 | 7/1987 |
| JP | 3221142 | 9/1991 |
| WO | WO 8902698 A1 | 4/1989 |
| WO | WO 9111977 A1 | 8/1991 |
| WO | WO 9112029 A1 | 8/1991 |
| WO | WO 9112030 A1 | 8/1991 |
| WO | WO 9619346 A2 | 6/1996 |
| WO | WO 9619346 A3 | 6/1996 |
| WO | WO 9725076 A1 | 7/1997 |
| WO | WO 9820915 A1 | 5/1998 |
| WO | WO 9826808 A2 | 6/1998 |
| WO | WO 9826808 A3 | 6/1998 |
| WO | WO 9947252 A3 | 9/1999 |
| WO | WO 0003797 A1 | 1/2000 |
| WO | WO 00/13764 A1 | 3/2000 |
| WO | WO 0029036 A2 | 3/2000 |
| WO | WO 0029036 A3 | 3/2000 |
| WO | WO 00/29036 * | 5/2000 |
| WO | WO 0059555 A1 | 10/2000 |
| WO | WO 0076558 A1 | 12/2000 |
| WO | WO 0106054 A1 | 1/2001 |
| WO | WO 0127368 A1 | 4/2001 |
| WO | WO 0226272 A1 | 4/2002 |
| WO | WO 0230204 A1 | 4/2002 |
| WO | WO 0249559 A2 | 6/2002 |
| WO | WO 02055115 A1 | 7/2002 |
| WO | WO 02062881 A2 | 8/2002 |
| WO | WO 02064877 A2 | 8/2002 |
| WO | WO 02064877 A3 | 8/2002 |
| WO | WO 02083297 A1 | 10/2002 |
| WO | WO 02084017 A1 | 10/2002 |
| WO | WO 02094329 A1 | 11/2002 |
| WO | WO 02095112 A1 | 11/2002 |
| WO | WO 03000979 A2 | 1/2003 |
| WO | WO 03025067 A1 | 3/2003 |
| WO | WO 03032959 A1 | 4/2003 |
| WO | WO 03088931 | 10/2003 |
| WO | WO 03092885 A1 | 11/2003 |
| WO | WO 2004 000986 A1 | 12/2003 |

OTHER PUBLICATIONS

Takagishi et al. J. Polym. Sci. Polym. Chem. Ed 1985, vol. 23, 2875-2878.*

Dowling et al. Macromolecules 1986, 19, 344-347.*
English Translation of JP 04-290547; 1992.*
Zezin et al. (Advances in Colloid and Interface Science (2009), doi:10.1016/j.cis.2009.09.002; 10 pages).*
Zezin et al. (High Energy Chemistry 2009, 43(2), pp. 100-104).).*
Abstract of SU834073, May 30, 1981.
PCT Search Report and Written Opinion for PCT/US2004/016933, Nov. 2, 2004.
Abstract of Japanese Patent No. 5106199, Apr. 27, 1993.
Abstract of Japanese Patent No. 9143872, Jun. 3, 1997.
Article—*Applicability of a SPME method for the Rapid Determination of VOCs*, Alexandre Béné, Jean-Luc Luisier, and Antoine Fornage, Chimia, vol. 56, No. 6, 2002, pp. 289-291.
Article—*Characterisation of novel modified active carbons and marine algal biomass for the selective adsorption of lead*, D.J. Malik, V. Strelko, Jr., M. Streat, and A.M. Puziy, Water Research, vol. 36, 2002, pp. 1527-1538.
Article—*Significance of Ammonia in the Genesis of Gastric Epithelial Lesions Induced by Helicobacter pylori: An in vitro Study with Different Bacterial Strains and Urea Concentrations*, P. Sommi, V. Ricci, R. Fiocca, M. Romano, K.J. Ivey, E. Cova, E. Solcia, and U. Ventura, Digestion, vol. 57, 1996, pp. 299-304.
Article—*Ammonia vapour in the mouth as a diagnostic marker for Helicobacter pylori infection: preliminary "proof of principle" pharmacological investigations*, C. D. R. Dunn, M. Black, D. C. Cowell, C. Penault, N. M. Ratcliffe, R. Spence, and C. Teare, British Journal of Biomedical Science, vol. 58, 2001, pp. 66-76.
Article—*Purification and Characterization of Urease from Helicobacter pylori*, Bruce E. Dunn, Gail P. Campbell, Guillermo I. Perez-Perez, and Martin J. Blaser, The Journal of Biological Chemistry, vol. 265, No. 16, Jun. 5, 1990, pp. 9464-1990.
Article—*Validation of $^{13}C$-Urea Breath Test for the Diagnosis of Helicobacter pylori Infection in the Singapore Population*, T. S. Chua, K. M. Fock, E. K. Teo, T. M. Ng, Singapore Medical Journal, vol. 43, No. 8, 2002, pp. 408-411.
Article—*Significance of ammonia produced by Helicobacter pylori*, Shigeji Ito, Yoshihiro Kohli, Takuji Kato, Yoshimichi Abe, and Takashi Ueda, European Journal of Gastroenterology & Hepatology, vol. 6, No. 2, 1994, pp. 167-174.
Article—*Spectrophotometric Assay of Thiols*, Peter C. Jocelyn, Methods in Enzymology, vol. 142, 1987, pp. 44-67.
Article—*Immunization of mice with peptomers covalently couopled to aluminum oxide nanoparticles*, Andreas Frey, Nicholas Mantis, Pamela A. Kozlowski. Alison J. Quayle, Adriana Bajardi, Juana J. Perdomo, Frank A. Robey, and Marian R. Neutra, Vaccine, vol. 17, 1999, pp. 3007-3019.
PCT Search Report for PCT/US03/39737, Jun. 18, 2004.
Abstract of Japanese Patent No. JP1262868, Oct. 19, 1989.
Abstract of Japanese Patent No. JP2157039, Jun. 15, 1990.
Abstract of Japanese Patent No. JP3195562, Aug. 27, 1991.
Abstract of Japanese Patent No. JP4335141, Nov. 24, 1992.
Abstract of Japanese Patent No. JP5261246, Oct. 12, 1993.
Abstract of Japanese Patent No. JP6285140, Oct. 11, 1994.
Abstract of Japanese Patent No. JP63072337, Apr. 2, 1988.
Abstract of Japanese Patent No. JP8152409, Jun. 11, 1996.
Abstract of Japanese Patent No. JP04255767, Sep. 10, 1992.
Abstract of Japanese Patent No. JP05098185, Apr. 20, 1993.
PCT Search Report for PCT/US03/32846, Jun. 7, 2004.
Article—*Adsorption of Dyes on Nanosize Modified Silica Particles*, Guangwei Wu, Athanasia Koliadima, Yie-Shein Her, and Egon Matijevic, Journal of Colloid and Interface Sciences, vol. 195, 1997, pp. 222-228.
Article—*Adsorption of Proteins and Antibiotics on Porous Alumina Membranes*, Yi Hua Ma, Aseem Bonsai, and William M. Clark, Fundamentals of Adsorption, vol. 80, 1992, pp. 389-396.
Quincy, III, et al., U.S. Appl. No. 10/723,761, filed Nov. 26, 2004, Odor Control In Personal Care Products.
MacDonald, et al., U.S. Appl. No. 10/955,316, filed Sep. 30, 2004, Odor-Reducing Quinone Compounds.
Article—*Saponins and Sapogenins. VIII. Surface Films of Echinocystic Acid and Derivatives*, C. R. Noller, J. Am. Chem. Soc., vol. 60, 1938, 3 pages.

Article—*Synthesis of porous Silica with help from cyclodextrin aggregates*, Markus Antonietti, Max-Planck-Institut für Kolloid-und, Germany, 1 page.
Article—*Immobilization of $(n-Bu_4N)_4W_{10}O_{32}$ on Mesoporous MCM-41 and Amorphous Silicas for Photocatalytic Oxidation of Cycloalkanes with Molecular Oxygen*, Andrea Maldotti, Alessandra Molinari, Graziano Varani, Maurizio Lenarda, Loretta Storaro, Franca Bigi, Raimondo Maggi, Alessandro Mazzacani, and Giovanni Sartori, Journal of Catalysis, vol. 209, 2002, pp. 210-216.
Article—*Fe-MCM-41 for Selective Epoxidation of Styrene with Hydrogen Peroxide*, Qinghong Zhang, Ye Wang, Satoko Itsuki, Tetsuya Shishido, and Katsuomi Takehira, The Chemical Society of Japan, Chemistry Letters 2001, pp. 946-947.
Article—*Mesoporous Sieves with Unified Hybrid Inorganic/Organic Frameworks*, Brian J. Melde, Brian T. Holland, Christopher F. Blanford, and Andreas Stein, Chem. Mater., vol. 11, No. 11, 1999, pp. 3302-3308.
Article—*From Cyclodextrin Assemblies to Porous Materials by Silica Templating*, Sebastian Polarz, Bernd Smarsly, Lyudmila Bronstein, and Markus Antonietti, Angew. Chem. Int., vol. 40, No. 23, 2001, pp. 4417-4421.
Paper—*Uniform Deposition of Ultrathin Polymer Films on the Surfaces of $Al_2O_3$ Nanoparticles by a Plasma Treatment*, Donglu Shi, S. X. Wang, Wim J. van Ooij, L. M. Wang, Jiangang Zhao, and Zhou Yu, University of Cincinnati and University of Michigan, Jun. 2000, pp. 1-15.
Article—*Development of novel dye-doped silica nanoparticles for biomarker application*, Swadeshmukul Santra, Kemin Wang, Rovelyn Tapec, and Weihong Tan, Journal of Biomedical Optics, vol. 6, No. 2, Apr. 2001, pp. 160-166.
Article—*Nanoparticles based on polyelectrolyte complexes: effect of structure and net charge on the sorption capability for solved organic molecules*, H.-M. Buchhammer, G. Petzold, and K. Lunkwitz, Colloid Polym. Sci., vol. 278, 2000, pp. 841-847.
Article—*Adsorption of Gases in Multimolecular Layers*, Stephen Brunauer, P.H. Emmett, and Edward Teller, The Journal of the American Chemical Society, vol. 60, Feb. 1938, pp. 309-319.
Article—*Study of the urea thermal decomposition (pyrolysis) reaction and importance to cyanuric acid production*, Peter M. Schaber, James Colson, Steven Higgins, Ed Dietz, Daniel Thielen, Bill Anspach, and Jonathan Brauer, American Laboratory, Aug. 1999, pp. 13-21.
Article—*The Colloid Chemistry of Silica*, American Chemical Society 200th National Meeting, Aug. 26-31, 1990, pp. 22-23 and pp. 52-59.
Article—*Structure and properties of silica nanoclusters at high temperatures*, I. V. Schweigert, K. E. J. Lehtinen, M. J. Carrier, and M. R. Zachariah, The American Physical Society, Physical Review B, vol. 65. No. 235410, pp. 1-9.
Article—*Grafting of Poly(ethylenimine) onto Mesylated Cellulose Acetate, Poly(methyl methacrylate) and Poly(vinyl chloride)*, Christopher J. Biermann and Ramani Narayan, Carbohydrate Polymers, vol. 12, 1990, pp. 323-327.
Abstract of Article—*Non-hydrothermal synthesis of copper-,-zinc- and copper-zinc hydrosilicates*, T. M. Yurieva, G. N. Kustova, T. P. Minyukova, E. K. Poels, A. Bliek, M. P. Demeshkina, L. M. Plyasova, T. A. Krieger, and V. I. Zaikovskii, Materials Research Innovations, vol. 5, No. 1, Jun. 2001, pp. 3-11.
Pocket Guide to Digital Printing, Frank Cost, Delmar Publishers, Albany, NY, ISBN 0-8273-7592-1, pp. 144-145.
Product Information Sheet on Snowtex®, 6 pages.
Lye, et al., U.S. Appl. No. 10/325,474, filed Dec. 20, 2002, Delivery System For Functional Compounds.
Quincy, III, et al., U.S. Appl. No. 10/328,730, filed Dec. 23, 2002, Odor Control Composition.
MacDonald, et al., U.S. Appl. No. 10/686,933, filed Oct. 16, 2003, Method For Reducing Odor Using Colloidal Nanoparticles.
McGrath, et al., U.S. Appl. No. 10/686,939, filed Oct. 16, 2003, Method For Reducing Odor Using Metal-Modified Particles.
Do, et al., U.S. Appl. No. 10/686,938, filed Oct. 16, 2003, Method For Reducing Odor Using Metal-Modified Silica Particles.
MacDonald, et al., U.S. Appl. No. 10/686,687, filed Oct. 16, 2003, Durable Charged Particle Coatings And Materials.

Urlaub, et al., U.S. Appl. No. 10/687,004, filed Oct. 16, 2003, High Surface Area Material Blends For Odor Reduction, Articles Utilizing Such Blends And Methods Of Using Same.

MacDonald, et al., U.S. Appl. No. 10/687,269, filed Oct. 16, 2003, Odor Controlling Article Including A Visual Indicating Device For Monitoring Odor Absorption.

MacDonald, et al., U.S. Appl. 10/687,270, filed Oct. 16, 2003, Visual Indicating Device For Bad Breath.

Boga, et al., U.S. Appl. No. 10/687,327, filed Oct. 16, 2003, Method And Device For Detecting Ammonia Odors And *Helicobacter pylori* Urease Infection.

Fish, et al., U.S. Appl. No. 10/687,425, filed Oct. 16, 2003, Odor Absorbing Extrudates.

\* cited by examiner

METHOD FOR REDUCING ODOR USING COORDINATED POLYDENTATE COMPOUNDS

BACKGROUND OF THE INVENTION

Odor control additives have been conventionally incorporated into substrates for a variety of reasons. For instance, U.S. Pat. No. 6,225,524 to Guarracino, et al. describes a substrate having an odor control composition that includes an absorbent gelling material and silica. Likewise, U.S. Pat. No. 6,376,741 to Guarracino, et al. describes a substrate having an odor control composition that includes silica and a zeolite (i.e., crystalline aluminosilicate). For instance, one type of silica said to be preferred in Guarracino, et al. ('524 patent) is amorphous silica having a particle size of 4-12 microns and a pore volume of 1-2 g/ml. Another type of preferred silica is said to be a silica gel having a medium pore diameter of from 90 to 110 angstroms, a surface area of from 250 $m^2/g$ to 350 $m^2/g$, and an average particle size of from 63 to 200 microns. Unfortunately, conventional odor control compositions, such as described above, have proven ineffective in obtaining the full level of odor control desired in many applications.

As such, a need exists for an odor control composition that may exhibit improved odor control properties, particularly when applied to a substrate.

SUMMARY OF THE INVENTION

In accordance with one embodiment of the present invention, a method for reducing odor is disclosed. The method comprises forming a coordination complex between a transition metal and a polydentate compound, and contacting the coordination complex with an odorous compound, such as mercaptans, ammonia, amines, sulfides, ketones, carboxylic acids, aldehydes, terpenoids, hexanol, heptanal, pyridine, etc. The transition metal provides one or more active sites for capturing the odorous compound. In some embodiments, the transition metal is selected from the group consisting of scandium, titanium, vanadium, chromium, manganese, iron, cobalt, nickel, copper, zinc, silver, gold, and combinations thereof.

The polydentate compound may vary depending on the desired application. For instance, the polydentate compound may be water-soluble and possess positively charged ligands to facilitate its application to certain types of substrates. The polydentate compound may contain one or more primary amines, secondary amines, tertiary amines, or combinations thereof. For example, the polydentate compound may be a polyalkylimine, such as polyethyleneimine, polypropyleneimine, or a dendrimer thereof. If desired, the polydentate compound may also be crosslinked. For example, a crosslinking agent selected from the group consisting of polyhydric alcohols, polyaziridines, epoxies, haloepoxies, polyaldehydes, polyisocyanates, and combinations thereof, may facilitate crosslinking.

In accordance with another embodiment of the present invention, an odor control composition is disclosed that comprises a coordination complex formed between a transition metal and, a polydentate compound. The transition metal is selected from the group consisting of scandium, titanium, vanadium, chromium, manganese, iron, cobalt, nickel, copper, zinc, silver, gold, and combinations thereof. The transition metal provides one or more active sites for capturing an odorous compound.

In accordance with still another embodiment of the present invention, a substrate for reducing odor is disclosed that is applied with an odor control composition that comprises a coordination complex formed between a transition metal and a polydentate compound. The transition metal is selected from the group consisting of scandium, titanium, vanadium, chromium, manganese, iron, cobalt, nickel, copper, zinc, silver, gold, and combinations thereof, the transition metal providing one or more active sites for capturing an odorous compound. In one embodiment, the substrate may be incorporated into an absorbent article. For instance, the absorbent article may include a liquid-transmissive liner, a liquid-transmissive surge layer, a liquid-absorbent core, and a vapor-permeable, liquid-impermeable outer cover, where the substrate forms at least a portion of the liner, surge layer, absorbent core, outer cover, or combinations thereof. In another embodiment, the substrate may be incorporated into a paper product, such as a facial tissue, bath tissue, paper towel, etc., or a facemask.

Other features and aspects of the present invention are discussed in greater detail below.

DETAILED DESCRIPTION OF REPRESENTATIVE EMBODIMENTS

Definitions

As used herein, a "coordinate bond" refers to a shared pair of electrons between two atoms, wherein one atom supplies both electrons to the pair.

As used herein, a "covalent bond" refers to a shared pair of electrons between two atoms, wherein each atom supplies one electron to the pair.

As used herein, the term "zeta potential" refers to the potential gradient that arises across an interface. Zeta potential measurements may be taken using, for instance, a Zetapals instrument available from the Brookhaven Instrument Corporation of Holtsville, N.Y. For example, zeta potential measurements may be conducted by adding one to three drops of a sample into a cuvet containing 1 millimolar KCl solution, using the instrument's default functions preset for aqueous solutions.

As used herein, an "absorbent article" refers to any article capable of absorbing water or other fluids. Examples of some absorbent articles include, but are not limited to, personal care absorbent articles, such as diapers, training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Materials and processes suitable for forming such absorbent articles are well known to those skilled in the art.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblowing" refers to a process in which fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S.

Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonding" refers to a process in which small diameter substantially continuous fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

In general, the present invention is directed to an odor control composition that includes a transition metal, such as scandium, titanium, vanadium, chromium, manganese, iron, cobalt, nickel, copper, zinc, silver, gold, etc. Single metallic, as well as dimeric, trinuclear, and cluster systems may be used. Without being limited by theory, it is believed that the transition metal provides one or more active sites for capturing and/or neutralizing an odorous compound. For example, the transition metal may be effective in removing odorous compounds, such as mercaptans (e.g., ethyl mercaptan), ammonia, amines (e.g., trimethylamine (TMA), triethylamine (TEA), etc.), sulfides (e.g., hydrogen sulfide, dimethyl disulfide (DMDS), etc.), ketones (e.g., 2-butanone, 2-pentanone, 4-heptanone, etc.) carboxylic acids (e.g., isovaleric acid, acetic acid, propionic acid, etc.), aldehydes, terpenoids, hexanol, heptanal, pyridine, and combinations thereof. If desired, more than one type of transition metal may also be utilized. This has an advantage in that certain metals may be better at removing specific odorous compounds than other metals. For example, copper may be more effective in removing sulfur and amine odors, while manganese may be more effective in removing carboxylic acids.

In accordance with the present invention, a polydentate compound is also employed that acts as a chelating agent for complexing with the transition metal. "Polydentate compounds" are macromolecular compounds having multiple ligands that may sometimes be ionizable when dissolved in a suitable solvent (e.g., water, alcohols, etc.). These macromolecular compounds may be, for instance, polymers, hyperbranched polymers, dendrimers, oligomers, etc. The molecular weight of the compounds may be from about 1,000 daltons to about 1 million daltons, in some embodiments from about 3,000 to about 200,000 daltons, and in some embodiments, from about 5,000 to about 50,000 daltons.

The polydentate compound may contain one or more ligands that are positively charged (cationic), negatively charged (anionic), and/or neutral. For instance, water-soluble polydentate compounds having one or more basic reactive ligands, such as amine or imine ligands, may be used. For instance, examples of suitable basic reactive ligand-containing polydentate compounds may include, but are not limited to, polylysine, polyvinylamine, polyallylamine, polyalkylimine, etc. Polyalkylimines, for example, are water-soluble, hydrophilic, polyamines evolved from aziridine and azetidine monomers, such as 1-unsubstituted imines, 1-substituted basic imines, activated imines (1-acyl substituted imines), isomeric oxazolines/oxazines, and so forth. Polyalkylimines may be linear or highly branched, thereby possessing primary, secondary, and tertiary amine groups. In one particular embodiment, the polyalkylimine is polyethyleneimine, which can be either linear or branched. Linear polyethyleneimine may be prepared via hydrolysis of poly(2-ethyl-2-oxazoline), while branched polyethyleneimine may be prepared by cationic chain-growth polymerization, either alone or with other monomers suitable for copolymerization with ethyleneimine.

Other suitable polyalkylimines include, but are not limited to, polypropyleneimine, as well as dendrimers, such as polypropyleneimine tetraamine (available from Aldrich Chemical under the name Generation 1.0, DAB-Am-4, contains 4 amino end groups), polypropyleneimine octaamine (available from Aldrich Chemical under the name Generation 2.0, DAB-Am-8, contains 8 amino end groups), polypropyleneimine hexadecaamine (available from Aldrich Chemical under the name Generation 3.0, DAB-Am-16, contains 16 amino end groups), polypropylene dotriacontaamine (available from Aldrich Chemical under the name Generation 4.0, DAB-Am-32, contains 32 amino end groups), and polypropyleneimine tetrahexacontaamine (available from Aldrich Chemical under the name Generation 5.0, DAB-Am-64, contains 64 amino end groups). Still other suitable examples of polydentate compounds include, but are not limited to, epichlorohydrin-functionalized polyamines and/or polyamidoamines, such as poly(dimethylamine-co-epichlorohydrin); polydiallyidimethyl-ammonium chloride; cationic cellulose derivatives, such as cellulose copolymers or cellulose derivatives grafted with a quaternary ammonium water-soluble monomer; polysaccharides; chitosan; and so forth.

Still other examples of suitable polydentate compounds include, but are not limited to, polyacrylic acids, such as poly(ethylene-co-methacrylic acid, sodium salt). It should also be understood that other polydentate compounds may also be utilized in the present invention, such as amphiphilic polydentate compounds (i.e., having polar an non-polar portions). For instance, some examples of suitable amphiphilic polydentate compounds include, but are not limited to, poly (styryl-b-N-methyl 2-vinyl pyridinium iodide) and poly (styryl-b-acrylic acid). Other suitable examples of polydentate compounds that may be used in the present invention are described in U.S. Pat. No. 5,807,636 to Sheu, et al. and U.S. Pat. No. 6,060,410 to Gillberg-LaForce, et al., which are incorporated herein in their entirety by reference thereto for all purposes.

In some instances, the polydentate compound selected for a particular application may vary depending on the nature of the substrate to which it may be applied. For example, the distributed charge of a polydentate compound may allow it to bind to substances having an opposite charge. Thus, polydentate compounds having positively charged ligands may bind more readily to substrates that are negatively charged, while polydentate compounds having negatively charged ligands may more readily bind to substrates that are positively charged. In one particular embodiment, for example, a polydentate compound having positively charged ligands is able to readily bond with a cellulosic fibrous substrate, which possesses a negative charge due to the hydroxy and/or carboxyl groups contained on its surface. The cellulose may also provide multiple hydrogen binding sites for bonding with the polydentate compound.

Regardless of the polydentate compound selected, the transition metal may be combined with therewith in a variety of ways. For instance, water-soluble polydentate compounds, such as polyethyleneimine, may simply be dissolved in water, and then mixed with a solution containing the appropriate transition metal in the form of a salt, such as those containing a copper ion ($CU^{+2}$), silver ion ($Ag^+$), gold ion ($Au^+$ and $Au^{+3}$), iron (II) ion ($Fe^{+2}$), iron (III) ion ($Fe^{+3}$), and so forth. If desired, surfactants may be utilized to disperse the polydentate compound in water or another solvent. For example, suitable surfactants may include, but are not limited to, Triton® X100, a nonionic surfactant available from Union Carbide, and Tergitol® 15-S40, an ethoxylated alcohol surfactant available from BASF.

When mixed with a transition metal, chelating moieties of the polydentate compound may form coordinate bonds with the transition metal and thus form a coordination complex. The chelating moieties may include, for instance, hydroxyl, carboxy, imino, amino (e.g. primary amines, secondary amines, or tertiary amines), carbonyl, phosphines, etc. The ratio of the polydentate compound to the transition metal may be selectively varied to achieve the desired results. In most embodiments, for example, the ratio of the polydentate compound to the transition metal is from about 0.1 to about 50, in some embodiments from about 0.5 to about 5, and in some embodiments, from about 1 to about 2.

In one embodiment, for example, polyethyleneimine is complexed to the transition metal. Polyethyleneimine contains multiple primary, secondary and tertiary amino groups that act in concert to coordinate transition metal ions. These compounds possess the ability to coordinate one metal ion per repeat unit, and thus may provide a high density of coordinated transition metal ions. One example of the coordination complex formed between polyethyleneimine and copper (derived from copper chloride) is set forth below:

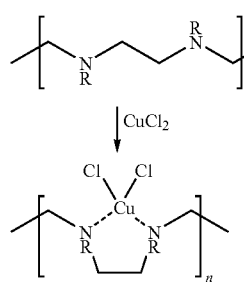

where R is either a hydrogen atom or continuation of the polymer chain.

One particular benefit of the present invention is that the coordinated polydentate complex may have a positive charge, which may be due to the positive charge on the polydentate compound, the positive charge of the transition metal, or both. By possessing a positive charge, the coordinated polydentate compound complex may be easily affixed to substrates that carry a negative surface charge through ionic attraction. Cellulosic fibrous materials, for instance, often contain hydroxy and/or carboxyl groups that result in a negative surface charge. Thus, the coordinated polydentate compound complex may form an electrostatic bond with these materials, and thus remain affixed thereto without the need for chemical binders or other attachment structures.

Despite being able to form a relatively strong bond with a substrate based on electrostatic attraction, water-soluble polydentate compounds sometimes become removed from a substrate when contacted with water. This may be problematic in applications where the presence of free metals is particularly disruptive. Thus, the polydentate compound may be crosslinked using various well-known techniques to render it water-insoluble and thus more resistant to removal from a substrate.

In some embodiments, for example, a chemical crosslinking agent may be used to facilitate crosslinking of the polydentate compound. The amount of the crosslinking agent may generally vary as desired. In some embodiments, the ratio of the crosslinking agent to the polydentate compound is from about 0.001 to about 5, in some embodiments from about 0.05 to about 1, and in some embodiments, from about 0.01 to about 0.25. The polydentate compounds may, for instance, be crosslinked with crosslinking agents, such as polyhydric alcohols (e.g., glycerol); polyaziridine compounds (e.g., 2,2-bishydroxymethyl butanoltris[3-(1-aziridine) propionate]); epoxy compounds; haloepoxy compounds (e.g., epicholorhydrin); polyaldehyde compounds (e.g., glutaraldehyde, glyoxal, malonaldehyde, succinaldehyde, adipaldehyde, and dialdehyde starch); polyisocyanate compounds (e.g., 2,4-toluene diisocyanate); etc. Still other suitable crosslinking agents are described in U.S. Pat. No. 5,102,597 to Roe; U.S. Pat. No. 5,308,641 to Cahalan, et al.; U.S. Pat. No. 5,536,254 to Hsuch, et al.; U.S. Pat. No. 6,339,714 to Huang, et al.; and WO 01/27368 to Smith, et al., which are incorporated herein in their entirety by reference thereto for all purposes.

In one particular embodiment, a polyalkylimine, for instance, may be crosslinked using an epoxy crosslinking agent having two or more epoxide groups per molecule. For example, the epoxy crosslinking agent may be a resin having end groups of the following formula:

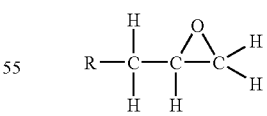

wherein, the end groups are directly attached to atoms of carbon, oxygen, nitrogen, sulfur or phosphorus, and mixtures thereof. For example, R may be bisphenol-A. At elevated temperatures, the epoxy crosslinking agent may crosslink the polyalkylimine between amino groups. The crosslinks are formed through attack by the amine proton at the epoxide rings, which opens the epoxide ring and forms an —OH group, thereby covalently crosslinking the amine (or amide) and terminal epoxide carbon. The resulting crosslinked network of the polyalkylimine is water-insoluble and may thus adhere tightly to the substrate even when contacted with water.

Examples of some suitable epoxy crosslinking agents include, but are not limited to, polyglycidyl ethers obtainable by reaction of a compound containing at least two free alcoholic hydroxyl and/or phenolic hydroxyl groups per molecule with epichlorohydrin under alkaline conditions. These polyglycidyl ethers may be made from acyclic alcohols, such as ethylene glycol, diethylene glycol, and higher poly(oxyethylene) glycols; cycloaliphatic alcohols, such as cyclohexanol and 1,2-cyclohexanediol; alcohols having aromatic nuclei, such as N,N-bis(2-hydroxyethyl)aniline; mononuclear phenols, such as resorcinol and hydroquinone; and polynuclear phenols, such as bis(4-hydroxyphenyl)methane, 4,4'-dihydroxydiphenyl, bis(4-hydroxyphenyl) sulphone, 1,1,2,2-tetrakis(4-hydroxyphenyl)ethane, and 2,2,-bis(4-hydroxyphenyl)propane (otherwise known as bisphenol A). In one particular embodiment, the epoxy crosslinking agent is a bisphenol-A glycidyl ether terminated resin.

In another particular embodiment, a polyalkylimine may be crosslinked using another polyalkylimine that is substituted with an epichlorohydrin group. One example of such a compound is commercially available from BASF under the trade name of "Lupasol SC-86X", and has the structure shown below:

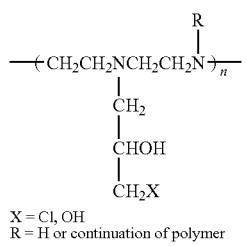

X = Cl, OH
R = H or continuation of polymer

Once the crosslinking agent is applied, the polydentate compound may then be cured at elevated temperatures. For instance, curing may be initiated by heating the polydentate compound and crosslinking agent to a temperature of from about 25° C. to about 150° C., in some embodiments from about 50° C. to about 120° C., and in some embodiments from about 70° C. to about 100° C., for a period of time of from about 1 minute to about 12 hours, in some embodiments from about 5 minutes to about 5 hours, and in some embodiments, from about 10 minutes to about 1 hour.

Besides using chemical crosslinking agents, the polydentate compound may also be crosslinked using other well-known techniques. For example, crosslinking may be induced with ionizing radiation, which is radiation having an energy sufficient to either directly or indirectly produce ions in a medium. Some suitable examples of ionizing radiation that may be used in the present invention include, but are not limited to, electron beam radiation, natural and artificial radio isotopes (e.g., α, β, and γ rays), x-rays, neutron beams, positively charged beams, laser beams, and so forth. Electron beam radiation, for instance, involves the production of accelerated electrons by an electron beam device. Electron beam devices are generally well known in the art. For instance, in one embodiment, an electron beam device may be used that is available from Energy Sciences, Inc., of Woburn, Mass. under the name "Microbeam LV." Other examples of suitable electron beam devices are described in U.S. Pat. No. 5,003,178 to Livesay; U.S. Pat. No. 5,962,995 to Avnery; U.S. Pat. No. 6,407,492 to Avnery, et al., which are incorporated herein in their entirety by reference thereto for all purposes.

Regardless of the technique utilized, crosslinking is believed to render the polydentate compound water-insoluble, and thus enhance its adherence to the surface of a substrate when contacted with water. In some embodiments, however, it may be desired to also bond the polydentate compound to a substrate. This further enhances the strength of the bond formed with the substrate, and thus reduces the likelihood that any free metal will be present during use. For instance, one method for bonding the polydentate compound to a substrate is to chemically "graft" the polydentate compound to a molecule on the substrate, thereby forming a covalent bond. One method of chemical grafting a polydentate compound onto cellulosic fibers (or derivatives thereof) may, for instance, involve nucleophilic displacement reactions as described in *Carbohydrate Polymers*, Biermann and Narayan, 12, 323-327 (1990), which is incorporated herein in its entirety by reference thereto for all purposes. For instance, polyethyleneimine may be grafted to mesylated cellulose acetate through a second order nucleophilic displacement reaction of mesylate groups by the primary amine groups of the polyethyleneimine.

The coordination complex of the present invention is believed to achieve high levels of odor reduction. For example, in some embodiments, the complex contains one or more free active sites capable of adsorbing an odorous compound. The complex, however, does not necessarily require the presence of free active sites. For example, one or more of the occupied active sites may be weak enough so that they are replaced by an odorous molecule when contacted therewith. Sulfur-based ligands, for instance, are normally weaker in their binding abilities than nitrogen and phosphine ligands, and thus, may sometimes be replaced by an odorous molecule.

Although the coordination complex of the present invention is capable of achieving high levels of odor reduction, it is sometimes desired to further enhance the level of odor reduction through the use of high-surface area particles as a carrier for the complex. When utilized, the high surface area of such particles may provide a further method of reducing odor. The particles may be formed from a variety of materials, including, but not limited to, silica, alumina, zirconia, magnesium oxide, titanium dioxide, iron oxide, zinc oxide, copper oxide, organic compounds such as polystyrene, and combinations thereof. The particles may have a surface area of from about 50 square meters per gram ($m^2/g$) to about 1000 $m^2/g$, in some embodiments from about 100 $m^2/g$ to about 600 $m^2/g$, and in some embodiments, from about 180 $m^2/g$ to about 240 $m^2/g$. Surface area may be determined by the physical gas adsorption (B.E.T.) method of Bruanauer, Emmet, and Teller, Journal of American Chemical Society, Vol. 60, 1938, p. 309, with nitrogen as the adsorption gas.

The particles may possess various forms, shapes, and sizes depending upon the desired result. For instance, the particles may be in the shape of a sphere, crystal, rod, disk, tube, string, etc. The average size of the particles is generally less than about 500 microns, in some embodiments less than about 100 microns, in some embodiments less than about 100 nanometers, in some embodiments from about 1 to about 50 nanometers, in some embodiments from about 2 to about 50 nanometers, and in some embodiments, from about 4 to about 20 nanometers. As used herein, the average size of a particle refers to its average length, width, height, and/or diameter. If desired, the particles may also be relatively nonporous or solid. That is, the particles may have a pore volume that is less than about 0.5 milliliters per gram (ml/g), in some embodiments less than about 0.4 milliliters per gram, in some embodiments less than about 0.3 ml/g, and in some embodiments, from about 0.2 ml/g to about 0.3 mug. Without intending to be limited by theory, it is believed that particles having such a small size and high surface area may improve the adsorption capability for many odorous compounds. Moreover, it is believed that the solid nature, i.e., low pore volume, of the particles may enhance the uniformity and stability of the particles, without sacrificing their odor adsorption characteristics.

Regardless of the material used to form the particles, the particles often possess a "zeta potential" that is opposite to the coordination complex. Although not required, the use of particles having an opposite zeta potential to the complex may facilitate the binding of the particles to the complex through ionic interaction. For example, in some embodiments of the present invention, the particles may have a negative zeta potential of about 0 millivolts (mV) or less, in some embodiments about −10 mV or less, and in some embodiments, about −20 mV or less. By possessing a negative surface charge, the particles are well suited for being affixed to polydentate compounds and/or transition metals that carry a positive charge. Depending upon the difference in charge, this attraction may be relatively permanent and substantive.

In one particular embodiment, for example, the particles are formed from silica particles having a negative zeta potential. Commercially available examples of silica nanoparticles, such as described above, include Snowtex-C, Snowtex-O, Snowtex-PS, and Snowtex-OXS, which are available from Nissan Chemical of Houston, Tex. Snowtex-OXS particles, for instance, have a particle size of from 4 to 6 nanometers, and may be ground into a powder having a surface area of approximately 509 square meters per gram.

Silica particles possess units that may or may not be joined together. Whether or not such units are joined generally depends on the conditions of polymerization. For instance, the acidification of a silicate solution may yield $Si(OH)_4$. If the pH of this solution is reduced below 7 or if a salt is added, then the units may tend to fuse together in chains and form a "gel." On the other hand, if the pH is kept at a neutral pH or above 7, the units may tend to separate and gradually grow to form a "sol." Silica particles may generally be formed according to any of a variety of techniques well known in the art, such as dialysis, electrodialysis, peptization, acid neutralization, and ion exchange. Some examples of such techniques are described, for instance, in U.S. Pat. No. 5,100,581 to Watanabe, et al.; U.S. Pat. No. 5,196,177 to Watanabe, et al.; U.S. Pat. No. 5,230,953 to Tsugeno, et al. and U.S. Pat. No. 5,985,229 to Yamada, et al., which are incorporated herein in their entirety by reference thereto for all purposes.

For exemplary purposes only, one embodiment of an ion-exchange technique for forming a silica sol will now be described in more detail. Initially, an alkali metal silicate is provided that has a molar ratio of silicon ($SiO_2$) to alkali metals ($M_2O$) of from about 0.5 to about 4.5. For instance, sodium water glass may be utilized that has a molar ratio of from about 2 to about 4. An aqueous solution of the alkali metal silicate is obtained by dissolving it in water at a concentration of, for instance, from about 2 wt. % to about 6 wt. %. The alkali metal silicate-containing aqueous solution may then be contacted with one or more ion-exchange resins. For instance, the solution may first be contacted with a strong-acid to ion-exchange all the metal ions in the aqueous solution. Examples of such strong acids include, but are not limited to, hydrochloric acid, nitric acid, sulfuric acid, and so forth. The contact may be accomplished by passing the aqueous solution through a column filled with the strong acid at a temperature of from about 0° C. to about 60° C., and in some embodiments, from about 5° C. to about 50° C. After passing through the column, the resulting silicic acid-containing aqueous solution may have a pH value of from about 2 to about 4. If desired, another strong acid may be added to the silicic acid-containing aqueous solution to convert the impurity metal components into dissociated ions. This additional strong acid may decrease the pH value of the resulting solution to less than about 2, and in some embodiments, from about 0.5 to about 1.8.

The metal ions and the anions from the strong acid may be removed from the solution by consecutive application of a strong acid (i.e., cation-exchange resin) and strong base (an-ion-exchange resin). Examples of suitable strong bases include, but are not limited to, sodium hydroxide, potassium hydroxide, and so forth. As a result of this consecutive application, the silicic acid-containing aqueous solution may have a pH value of from about 2 to about 5. This acidic aqueous solution may then be contacted with one or more additional strong bases to stabilize the solution at a pH value of from about 7 to about 9.

The stabilized silicic acid-containing aqueous solution is then fed to a container in which the liquid temperature is maintained at from about 70° C. to about 100° C. This process results in an increase in concentration of the silica to from about 30 wt. % to about 50 wt. %. The stable aqueous silica sol may then be consecutively contacted with a strong acid and strong base, such as described above, so that the resulting aqueous silica sol is substantially free from polydentate metal oxides, other than silica. Finally, ammonia may be added to the aqueous sol to further increase its pH value to from about 8 to about 10.5, thereby forming a stable aqueous silica sol having a silica concentration of from about 30 wt. % to about 50 wt. %, a mean particle size of from about 10 to about 30 nanometers, and that is substantially free from any polydentate metal oxides, other than silica.

When utilized, the amount of particles may generally vary in relation to the transition metal and polydentate compound. For example, the ratio of the particles to the polydentate compound may be from about 10 to about 10,000, in some embodiments from about 50 to about 5,000, and in some embodiments, from about 100 to about 1,000. Generally speaking, the order in which the particles, polydentate compound, and transition metal are mixed may be varied as desired. In some instances, the order of mixing may actually affect the characteristics of the particles. In some embodiments, for example, it may be desired to first mix the polydentate compound with the transition metal, and then mix the resulting coordination complex with the particles.

If desired, the odor control composition of the present invention may be applied to a substrate. The substrate may provide an increased surface area to facilitate the adsorption of odorous compounds by the complex. In addition, the substrate may also serve other purposes, such as water absorption. Any of a variety of different substrates may be incorporated with the odor control composition in accordance with the present invention. For instance, nonwoven fabrics, woven fabrics, knit fabrics, wet-strength paper, film, foams, etc., may be applied with the odor control composition. When utilized, the nonwoven fabrics may include, but are not limited to, spunbonded webs (apertured or non-apertured), melt-blown webs, bonded carded webs, air-laid webs, coform webs, hydraulically entangled webs, and so forth.

In some embodiments, for example, the odor control composition may be utilized in a paper product containing one or more paper webs, such as facial tissue, bath tissue, paper towels, napkins, and so forth. The paper product may be single-ply in which the web forming the product includes a single layer or is stratified (i.e., has multiple layers), or multi-ply, in which the webs forming the product may themselves be either single or multi-layered. Normally, the basis weight of such a paper product is less than about 120 grams per square meter (gsm), in some embodiments less than about 80 gsm, in some embodiments less than about 60 grams per square meter, and in some embodiments, from about 10 to about 60 gsm.

Any of a variety of materials can also be used to form the paper web(s) of the product. For example, the material used to make the paper product may include fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Kimberly-Clark Corporation under the trade designations "Longlac-19". Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, and so forth. In addition, in some instances, synthetic fibers can also be utilized. Some suitable synthetic fibers can include, but are not limited to, rayon fibers, ethylene vinyl alcohol copolymer fibers, polyolefin fibers, polyesters, and so forth.

If desired, the substrate may form all or a portion of an absorbent article. In one embodiment, for instance, the absorbent article includes a liquid-transmissive bodyside liner, a liquid-transmissive surge layer below the bodyside liner, a liquid-absorbent core below the surge layer, and a moisture vapor permeable, liquid impermeable outer cover below the absorbent core. A substrate treated with the odor control composition of the present invention may be employed as any one or more of the liquid transmissive (non-retentive) and absorbent layers. An absorbent core of the absorbent article, for instance, may be formed from an absorbent nonwoven web that includes a matrix of hydrophilic fibers. In one embodiment, the absorbent web may contain a matrix of cellulosic fluff fibers. One type of fluff that may be used in the present invention is identified with the trade designation CR1654, available from U.S. Alliance, Childersburg, Ala., U.S.A., and is a bleached, highly absorbent sulfate wood pulp containing primarily soft wood fibers. In another embodiment, the absorbent nonwoven web may contain a hydoentangled web. Hydroentangling processes and hydroentangled composite webs containing various combinations of different fibers are known in the art. A typical hydroentangling process utilizes high pressure jet streams of water to entangle fibers and/or filaments to form a highly entangled consolidated fibrous structure, e.g., a nonwoven fabric. Hydroentangled nonwoven fabrics of staple length fibers and continuous filaments are disclosed, for example, in U.S. Pat. No. 3,494,821 to Evans and U.S. Pat. No. 4,144,370 to Bouolton, which are incorporated herein in their entirety by reference thereto for all purposes. Hydroentangled composite nonwoven fabrics of a continuous filament nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes.

Another type of suitable absorbent nonwoven web is a coform material, which is typically a blend of cellulose fibers and meltblown fibers. The term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

If desired, the absorbent nonwoven web may also contain a superabsorbent material. Superabsorbents have the ability to absorb a great amount of fluid in relation to their own weight. Typical superabsorbents used in sanitary napkins may absorb anywhere from about 5 to about 60 times their weight in blood. Superabsorbent materials are produced in a wide variety of forms including, but not limited to, particles, fibers and flakes. Superabsorbents having a high mechanical stability in the swollen state, an ability to rapidly absorb fluid, and those having a strong liquid binding capacity, typically perform well in absorbent articles. Hydroxyfunctional polymers have been found to be good superabsorbents for this application. For example, a hydrogel-forming polymer, such as a partially neutralized cross-linked copolymer of polyacrylic acid and polyvinyl alcohol, may be utilized. After the polymer is formed, it is mixed with about a 1% anhydrous citric acid powder. The citric acid has been found to increase the ability of the superabsorbent to absorb menses and blood. This is particularly beneficial for use in a sanitary napkin or other feminine pads. The finely ground, anhydrous citric acid powder, which is void of water, along with trace amounts of fumed silica, is mixed with the polymer that may have been screened to an appropriate particle size. This mixture may also be formed into a composite or a laminate structure. Such superabsorbents may be obtained from Dow Chemical and Stockhausen, Inc., among others. This superabsorbent is a partially neutralized salt of cross-linked copolymer of polyacrylic acid and polyvinyl alcohol having an absorbency under load value above about 25. Some suitable superabsorbents are described in U.S. Pat. No. 4,798,603 to Meyers, et al., Re. 32,649 to Brandt, et al. and U.S. Pat. No. 4,467,012 to Pedersen, et al., U.S. Pat. Nos. 4,604,313 and 4,655,757 to McFarland, et al., U.S. Pat. No. 6,387,495 to Reeves, et al., as well as in published European Patent Application 0,339,461 to Kellenberger.

As indicated above, the odor control composition may also be applied to a liquid transmissive layer of the absorbent article, such as the bodyside liner or surge layer. Such liquid transmissive layers are typically intended to transmit liquid quickly, and thus generally do not retain or absorb significant quantities of aqueous liquid. Materials that transmit liquid in such a manner include, but are not limited to, thermoplastic spunbonded webs, meltblown webs, bonded carded webs, air laid webs, and so forth. A wide variety of thermoplastic materials may be used to construct these non-retentive nonwoven webs, including without limitation polyamides, polyesters, polyolefins, copolymers of ethylene and propylene, copolymers of ethylene or propylene with a $C_4$-$C_{20}$ alpha-olefin, terpolymers of ethylene with propylene and a $C_4$-$C_{20}$ alpha-olefin, ethylene vinyl acetate copolymers, propylene vinyl acetate copolymers, styrene-poly(ethylene-alpha-olefin) elastomers, polyurethanes, A-B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, poly-1-butene, copolymers of poly-1-butene including ethylene-1-butene copolymers, polybutadiene, isobutylene-isoprene copolymers, and combinations of any of the foregoing.

The amount of the odor control composition present on the substrate may vary depending on the nature of the substrate and its intended application. In some embodiments, for example, the dry, solids add-on level is from about 0.001% to about 20%, in some embodiments from about 0.01% to about 10%, and in some embodiments, from about 0.1% to about 4%. The "solids add-on level" is determined by subtracting the weight of the untreated substrate from the weight of the treated substrate (after drying), dividing this calculated weight by the weight of the untreated substrate, and then multiplying by 100%. Lower add-on levels may provide optimum absorbency or other characteristics of the substrate, while higher add-on levels may provide optimum odor reduction.

The odor control composition may be applied to a substrate using any of a variety of well-known application techniques. Suitable techniques for applying the composition to a substrate include printing, dipping, spraying, melt extruding, solvent coating, powder coating, and so forth. The odor control composition may be incorporated within the matrix of the substrate and/or applied to the surface thereof. For example, in one embodiment, the odor control composition is coated onto one or more surfaces of the substrate.

The percent coverage of the odor control composition on the surface may be selected to achieve the desired odor reduction. Typically, the percent coverage is greater than about 50%, in some embodiments greater than about 80%, and in some embodiments, approximately 100% of the area of a given surface. The present inventors have discovered that, even when applied uniformly (e.g., about 100% coverage) onto a surface of the substrate, the resulting substrate may still remain porous. For instance, the porosity of the coated substrate may enable it to still be used in application where liquid permeability is required, such as in absorbent articles. Also, the porosity of the coated substrate allows gaseous odorous compounds to flow therethrough, exposing the underside of the odor control composition (surface facing the substrate) to the odorous compound. In this manner, the entire surface area of the odor control composition is more effectively utilized for reducing odor. In most embodiments, the coated substrate exhibits a porosity such that about 20 cubic feet of air or greater may flow through 1 square foot of the substrate in 1 minute under an air pressure differential of 125 Pascals (0.5 inches of water). In other words, such a substrate is said to have an air permeability of about 20 cubic feet per minute (cfm) or greater. In some embodiments, the air permeability ranges from about 20 cfm to about 500 cfm, in some embodiments from about 50 cfm to about 400 cfm, and in some embodiments, from about 75 cfm to about 300 cfm, under an air pressure differential of 125 Pascals. Air permeability (volumetric air flow per square foot of material under an air pressure differential of 125 Pascals) may be measured in a variety of ways. For example, "Frazier Air Permeability" is determined according to Federal Test Standard 191A, Method 5450 with a Frazier Air Permeability Tester (Frazier Precision Instrument Co., Gaithersburg, Md.), and is reported as an average of 3 sample readings.

The odor control composition of the present invention is versatile and may also be used with other types of articles of manufacture. For instance, the odor control composition may be used in air filters, such as house filters, vent filters, disposable facemasks, and facemask filters. Exemplary facemasks, for instance, are described and shown, for example, in U.S. Pat. Nos. 4,802,473; 4,969,457; 5,322,061; 5,383,450; 5,553,608; 5,020,533; 5,813,398; and 6,427,693, which are incorporated herein in their entirety by reference thereto for all purposes. In one embodiment, a substrate coated with the odor control composition of the present invention may be utilized as a filtration layer of the facemask. Filtration layers, such as meltblown nonwoven webs, spunbond nonwoven webs, and laminates thereof, are well known in the art.

In another embodiment, the odor control composition may be applied to walls, wallpaper, glass, toilets, and/or countertops. For instance, the odor control composition may be used in a restroom facility. Other uses include, without limitation, refrigerator mats and fabric softener sheets.

The odor control composition may also be applied to water treatment systems for removing sulphurous compounds from well water or in toilet tanks to reduce the odors resulting from urine. The odor control composition may also be used in liquid detergents and household cleaners to remove odors. In another embodiment, the odor control composition is used as aerosol odor neutralizers/deodorants. The odor control composition is packaged with a propellant that allows spraying the odor control composition into the air for removal of gases and odorous compounds. The odor control composition may be used in a household air freshener or be used in combination with a mist emitted from a vaporizer or humidifier.

The effectiveness of the odor control composition of the present invention may be measured in a variety of ways. For example, the percent of an odorous compound adsorbed by the odor control composition may be determined in accordance with the headspace gas chromatography test set forth herein. In some embodiments, for instance, the odor control composition of the present invention is capable of adsorbing at least about 25%, in some embodiments at least about 45%, and in some embodiments, at least about 65% of a particular odorous compound. The effectiveness of the odor control composition in removing odors may also be measured in terms of "Relative Adsorption Efficiency", which is also determined using headspace gas chromatography and measured in terms of milligrams of odor adsorbed per gram of the odor control composition. It should be recognized that the surface chemistry of any one type of odor control composition may not be suitable to reduce all types of odors, and that low adsorption of one or more odorous compounds may be compensated by good adsorption of other odorous compounds.

The present invention may be better understood with reference to the following examples.

Test Methods

Quantitative and qualitative odor tests were used in the Examples. Quantitative odor adsorption was determined in the Example using a test known as "Headspace Gas Chromatography." Headspace gas chromatography testing was conducted on an Agilent Technologies 5890, Series II gas chromatograph with an Agilent Technology 7694 headspace sampler (Agilent Technologies, Waldbronn, Germany). Helium was used as the carrier gas (injection port pressure: 12.7 psig; headspace vial pressure: 15.8 psig; supply line pressure is at 60 psig). A DB-624 column was used for the odorous compound that had a length of 30 meters and an internal diameter of 0.25 millimeters. Such a column is available from J&W Scientific, Inc. of Folsom, Calif.

The operating parameters used for the headspace gas chromatography are shown below in Table 1:

TABLE 1

Operating Parameters for the Headspace Gas Chromatography Device.
Headspace Parameters

| Zone Temps, ° C. | Oven | 37 |
|---|---|---|
| | Loop | 42 |
| | TR. Line | 47 |
| Event Time, minutes | GC Cycle time | 10.0 |
| | Vial eq. Time | 10.0 |
| | Pressuriz. Time | 0.20 |
| | Loop fill time | 0.20 |
| | Loop eq. Time | 0.15 |
| | Inject time | 0.30 |
| Vial Parameters | First vial | 1 |
| | Last vial | 1 |
| | Shake | [off] |

The test procedure involved placing 150 milligrams of paper towels (or other substrates) coated with coordinated polydentate compound complex in a 20-cubic centimeter headspace vial. Using a syringe, an aliquot of the odorous compound was also placed in the vial. The vial was then sealed with a cap and a septum and placed in the headspace gas chromatography oven at 37° C. After two (2) hours, a hollow needle was inserted through the septum and into the vial. A 1-cubic centimeter sample of the headspace (air inside the vial) was then injected into the gas chromatograph.

Initially, a control vial with only the aliquot of odorous compound was tested to define 0% odorous compound adsorption. To calculate the amount of headspace odorous compound removed by the sample, the peak area for the odorous compound from the vial with the sample was compared to the peak area from the odorous compound control vial. Testing was done with 1 microliter of ethyl mercaptan (EtSH), 1 microliter of isovaleraldehyde (3-MB), 1 microliter of triethylamine (TEA), 28% ammonia hydroxide ($NH_3$), and/or ammonia generated by 10 microliters of urea and 100 microliters of urease. In some cases, the pure odorous compounds were dissolved in a solvent with a ten-fold dilution, and two or three microliters of the diluted solution was used as the odor in the headspace GC tests. Suitable solvents are ethyl alcohol, hexane, etc. Each sample was tested in triplicate.

Qualitative odor reduction was also assessed against common odors, such as garlic, cigarette and urine.

Example 1

The effectiveness of the odor control composition of the present invention to adsorb odorous compounds was demonstrated. A polyethyleneimine solution was initially prepared by dissolving 3.3 grams of branched polyethyleneimine (obtained from Polyscience, MW=10,000 daltons) in 900 milliliters of deionized water. Thereafter, 335 milligrams of copper chloride (obtained from Aldrich, 97 wt. %) was added to the polyethyleneimine solution. Upon addition of copper chloride, the solution turned deep blue, indicating the formation of a coordination complex. A piece of a Scott® paper towel was then immersed in the solution for 1 minute and allowed to dry in air. The solids add-on level was 5.8%. The product was tested for odor adsorption using 1 microliter of ethyl mercaptan (0.839 milligram) as described above. The % odor reduction was determined to be 85.4%. In a parallel test, a control sample (piece of untreated Scott® paper towel) reduced only 11.0% odor.

Example 2

The effectiveness of the odor control composition of the present invention to adsorb odorous compounds was demonstrated. A polyethyleneimine solution was initially prepared by dissolving 132.5 milligrams of branched polyethyleneimine (obtained from Polyscience, MW=1,800 daltons) in 105 milliliters of deionized water. 5 milliliters of this solution was mixed with 300 milliliters of 2% aqueous solution of Snowtex-O particles, which are colloidal silica nanoparticles commercially available from Nissan Chemical America of Houston, Tex. The particles have an average particle size of between 10 to 20 nanometers and a surface area between 180 to 240 square meters per gram. Thereafter, 275 milligrams of copper chloride (obtained from Aldrich) was added to the polyethyleneimine/silica suspension. Upon addition of copper chloride, the solution turned deep blue, indicating the formation of a coordination complex.

To test the effectiveness in which the copper chloride and polyethyleneimine were able to bind to the silica particles, the zeta potential of the silica particles was determined by increasing the amount of the combined volume of copper chloride and polyethyleneimine ("titrant") from 0 to about 75 milliliters. Prior to addition of the titrant, the silica particles had a zeta potential of about −60 millivolts (mV). At about 27 milliliters of total titrant volume, the zeta potential of the silica particles became positive (above 0). Finally, at about 75 milliliters of total titrant volume, the zeta potential of the silica particles was about +40 mV. The significant increase in zeta potential indicated a strong adherence of the polyethyleneimine and copper chloride to the surface of the particles.

Odor reduction effectiveness was also determined. Specifically, an aqueous suspension containing 2 wt. % of the Snowtex-O particles, 0.002 wt. % of the polyethyleneimine, 0.067 wt. % copper chloride, and water, and was coated onto a Kleenex® paper towel. The treated towel was then dried in air and under vacuum. The solids add-on was 7.5%. This product was tested for odor adsorption using 3 microliters of the diluted ethyl mercaptan solution in ethyl alcohol (net weight of ethyl mercaptan was 0.23 milligram) as described above. The % odor reduction was determined to be 92% and the relative adsorption efficiency was 32 milligrams of ethyl mercaptan adsorbed per gram of the substrate.

Example 3

The effectiveness of the odor control composition of the present invention to adsorb odorous compounds was demonstrated. A polyethyleneimine (PEI) solution was initially prepared by dissolving branched polyethyleneimine (obtained from Polyscience, MW=10,000 daltons) in deionized water to obtain solutions with varying polyethyleneimine concentrations. Thereafter, a metal salt was combined with the polyethyleneimine solution. Various metal salts were tested, including iron (III) chloride ($FeCl_3$), zinc sulfate ($ZnSO_4$), copper chloride ($CuCl_2$), and silver sulfadiazine (AgSDZ)

along with sodium benzoate (NaBZ) and sodium salicylate (NaSC). The salts were tested at various concentrations.

The PEI-metal complexes (copper, iron (III), and zinc) were prepared by simply dissolving the corresponding metal salts in the PEI solution. To prepare the PEI-Ag complex, 500 milligrams of AgSDZ, 1 gram of NaBZ, and 1 gram of NaSC were added to 1 liter of water. 10 grams of PEI (obtained from BASF, MW=25,000 daltons) were then slowly added to the mixture. After stirring for 24 hours, a PEI-Ag complex was obtained. Such a method for preparing the PEI-Ag complex is described in WO 02/30204 to Kim, which is incorporated herein in its entirety by reference thereto for all purposes. Unlike most unbound soluble silver salts, the PEI-Ag complex has excellent color stability.

Odor reduction was then tested as described above. For comparison, activated carbon particles were also tested. The activated carbon particles were placed in a headspace GC vial along with a piece of a Scott® paper towel. The paper towel weight was 150 milligrams and the amount of the activated carbon was approximately 4.5 milligrams. In addition, a plain Scott® paper towel was also tested without any odor-reducing compounds. The results are shown below in Table 2.

TABLE 2

Odor Reduction Results

| Sample | Color | % Solids Add-On Level | % EtSH Removed | % 3-MB Removed | % TEA Removed |
|---|---|---|---|---|---|
| Towel Only | White | 0 | 7.5 | 5.6 | 29.4 |
| Activated Carbon | Black | 3.0 | 82.7 | 96.4 | 100 |
| 0.16 wt. % PEI, 0.09 wt. % FeCl$_3$ | Deep Brown | 3.2 | 8.1 | 29.2 | 68.6 |
| 0.16 wt. % PEI, 0.14 wt. % ZnSO$_4$ | White | 13.7 | 44.6 | 10.0 | 100 |
| 0.66 wt. % PEI, 0.36 wt. % CuCl$_2$ | Blue | 9.4 | 90.1 | 24.3 | 34.4 |
| 0.33 wt. % PEI, 0.18 wt. % CuCl$_2$ | Blue | 5.8 | 85.4 | 22.0 | Not determined |
| 1 wt. % PEI, 0.05 wt. % AgSDZ, 0.1 wt. % NaBZ, 0.1 wt. % NaSC | Slightly Brown | 11.0 | 14.2 | 92.1 | 16.6 |

Thus, for these particular tests, the copper-containing samples had the best odor adsorption of ethyl mercaptan, but had a lower odor adsorption for the other odorous compounds. However, the silver-containing samples provided excellent odor adsorption for isovaleraldehyde, and the zinc-containing samples provided excellent odor adsorption for triethylamine. Because the samples had different amount of add-on levels, the results obtained may not necessarily be indicative of the selectivity for adsorbing odors in all cases.

A further qualitative test was also conducted on these samples. Specifically, a freshly cut piece of garlic was placed in separate glass jars containing approximately 200 milligrams of Scott® paper towels coated with the PEI-Cu, PEI-Fe, PEI-Zn, and PEI-Ag samples. These samples had solids add-on levels as shown above in Table 2. An additional piece of garlic was also placed in a glass jar containing approximately equal portions of Scott® paper towels coated with the PEI-Cu, PEI-Fe, PEI-Zn, and PEI-Ag samples, with the total weight equaling 200 milligrams. A plain paper towel was also tested for comparative purposes. The jars were sniffed by five (5) individuals and ranked based on odor-reduction. The glass jar containing the mixture of paper towels was observed to have the best odor reduction. All of the samples were determined to possess better odor adsorption than the control sample.

Example 4

The effectiveness of the odor control composition of the present invention to adsorb odorous compounds was demonstrated. Polypropyleneimine hexadecaamine (0.125 millimoles, 211 milligrams) (available from Aldrich Chemical under the name Generation 3.0, DAB-Am-16, contains 16 amino end groups) was initially dissolved in 150 milliliters of distilled water. The resulting solution was transferred to a 500-milliliter round bottom flask containing a stir bar. Copper nitrate (2 millimoles, 375 milligrams) was also separately dissolved in 50 milliliters of water. The copper nitrate solution was then added dropwise to the polypropyleneimine hexadecaamine solution under vigorous stirring. The solution turned a deep blue color, and was then allowed to stir for 24 hours at room temperature.

A Scott® paper towel was treated with the resulting solution by submerging it for 1 minute in the solution with agitation. The treated sample was dried under vacuum overnight at room temperature. The average solids add-on level was 3.44%. The product was then tested for odor adsorption of ammonia. Ammonia was generated by adding urease (10 microliters of a 10 milligram per milliliter solution at a pH of 7.4) to the sample and then soaking it with urea (100 microliters of a 4 molar urea solution at a pH of 7.4). The sample was then incubated at 31° C. for 2 hours and analyzed for ammonia content. A control sample was also tested that did not contain the copper-dendrimer complex. Based on the above, it was determined that the sample containing the copper-dendrimer complex had an odor reduction of approximately 99%.

Example 5

The effectiveness of the odor control composition of the present invention to adsorb odorous compounds was demonstrated. The same experimental procedures of Example 3 were used, except that the molar ratios of the PEI to the transitional metal were kept equal for each solution. Specifically, to obtain PEI-metal complexes with the same PEI/metal molar ratios, the metal salt was added in the following respective quantities:

CuCl$_2$—74 milligrams

ZnSO$_4$.7H$_2$O—228 milligrams

AgNO$_3$—94 milligrams

FeCl$_3$—90 milligrams.

The PEI-Ag complex was prepared by dissolving silver nitrate directly into the PEI solution. Specifically, 165 milligrams of PEI (obtained from Polyscience, MW=10,000 daltons) was dissolved in 500 milliliters of deionized water. Odor reduction was then tested as described above. The results are shown below in Table 3.

TABLE 3

Odor Reduction Results

| Sample | % Solids Add-On Level | % EtSH Removed | % 3-MB Removed | % TEA Removed |
|---|---|---|---|---|
| 0.033% PEI, 0.018% FeCl₃ | 2.9 | 13.4 | 27.2 | 76.3 |
| 0.033% PEI, 0.046% ZnSO₄ | 3.1 | 17.0 | 17.0 | 47.4 |
| 0.033% PEI, 0.018% CuCl₂ | 2.9 | 31.3 | 16.0 | 51.5 |
| 0.033% PEI, 0.019% AgNO₃ | 3.0 | 39.5 | 26.6 | 44.7 |

Example 6

The effectiveness of the odor control composition of the present invention to adsorb odorous compounds was demonstrated. 3.3 grams of PEI (obtained from Polyscience, MW=10,000) were dissolved in 500 milliliters of water. A PEI-Cu complex was formed by adding 1.8 grams of CuCl₂ to the PEI solution. A piece of a Scott® paper towel was immersed in the above solution for 1 minute and allowed to dry in the air. The treated paper towel was tested for odor reduction as described above in 1 microliter of 28% ammonia hydroxide. It was determined that the treated paper towel removed 92.7% of the odor.

Example 7

The effectiveness of the odor control composition of the present invention to adsorb odorous compounds was demonstrated. 250 milliliters of an aqueous solution containing 1.33% PEI (obtained from BASF, MW=25,000 Daltons) and 0.36% CUCl₂ were mixed with an ethanol solution containing 10% of 1,4-butanediol diglycidyl ether. The resulting solution contained 0.18% CuCl₂, 0.66% PEI, and 5% of the diepoxide. A piece of a Scott® paper towel (3318.1 milligrams) was immersed in the above solution, which was heated to boil (80-85° C.) for approximately one hour. The paper towel was subsequently washed with three portions of 200 milliliters of ethanol, followed by three portions of deionized water. The towel was then allowed to dry in air for 24 hours. The weight of the paper towel after treatment and drying was found to be 3436.4 milligrams, and therefore the solids add-on level was 3.6%.

150 milligrams of the paper towel was tested for odor reduction as described above using 1 microliter of ethyl mercaptan. It was determined that the paper towel had an odor reduction of 39.2%.

Example 8

The effectiveness of the odor control composition of the present invention to adsorb odorous compounds was demonstrated. A treating solution was prepared by dissolving 1 gram of PEI (Lupasol WF from BASF, MW=25,000 Daltons) and 500 milligrams of CuCl₂ in 200 milliliter of water, followed by adding 50 milliliters of a crosslinking agent (Lupasol SC-86X from BASF). A piece of a Scott® paper towel was soaked in the treating solution for 1 minute and hung in the fume hood for ten minutes to allow the liquid to drip. The wet towels were then transferred to an oven with a set temperature of 95° C. The towels were kept in the oven for approximately one hour, and were then washed with deionized water three times, followed by drying in air for 24 hours. The solids add-on level was 18.5%.

150 milligrams of the treated paper towel were tested for odor reduction as described above using 1 microliter of ethyl mercaptan. It was determined that the paper towel had an odor reduction of 19.5%. The Scott® paper towel was also subjected to qualitative sniffing tests against common odors, such as garlic, cigarette and urine.

Garlic Odor: A piece of the treated Scott® towel (approximately 200 milligrams) was placed in a jar containing a piece of freshly cut garlic and the jar was covered. The control contained a piece of untreated Scott® towel of the same size and the garlic. In approximately three hours, the garlic odor in the jar containing the treated towel was nearly eliminated, whereas the control still smelled strongly.

Cigarette Odor: A similar test was carried out with cigarette odor. A square of a Scott® towel was placed in a jar containing three used cigarettes for 24 hours. The towel was transferred to an empty jar, and a piece of the treated Scott® towel (approximately 200 milligrams) was placed on top. In approximately 5 hours, the cigarette odor was found to have diminished (but not completely disappeared), while the control still had a strong odor.

Urine Odor: A piece of the treated Scott® paper towel (approximately 200 milligrams) was inserted into an incontinence pad (a Poise® pad available from Kimberly-Clark Corporation) on which 60 milliliters of freshly collected urine was applied. The same amount of the urine sample was also applied to a control pad that did not contain the treatment. Both pads were incubated at 32° C. for 24 hours, and a sniffing test was then conducted. It was determined that the pad with the insert had reduced odor compared with the control.

Example 9

A piece of Scott® paper towel of the same size as described in Example 8 was immersed in 0.1 wt % CuCl₂ solution for 1 minute and allowed to dry in air. The add-on level was 2.8%. Another piece of Scott® paper towel was immersed in an aqueous solution containing 0.1% CuCl₂ and 0.66% PEI (from BASF, MW=25,000 Daltons). The paper towel was allowed to dry in the air. The paper towels, along with those obtained in Examples 7 and 8, were immersed for 24 hours in separate beakers, each containing 30 milliliters of deionized water. The approximate weight of each paper towel was 870 milligrams. The supernatants were filtered to remove fibers detached and analyzed for the content of the leached copper. The content of copper was determined by ICP-Optical Emission Spectroscopy. Table 4 below summarizes the test results.

TABLE 4

Leaching of Copper and Nitrogen

| Sample | Copper Content in Supernatant (mg/L) |
|---|---|
| CuCl₂ coated Scott ® towel | 37.00 |
| PEI-Cu coated Scott ® towel | 15.00 |
| PEI-Cu of Example 7 | 0.37 |
| PEI-Cu of Example 8 | 2.70 |

Example 10

The effectiveness of the odor control composition of the present invention to adsorb odorous compounds was demonstrated. A treating solution was prepared by dissolving 1.8 grams of PEI (Lupasol WF from BASF, MW=25,000 Daltons) and 1.08 grams of $CuCl_2$ in 300 ml water, followed by adding 2.0 milliliters of a crosslinking agent (Lupasol SC-86X from BASF). A piece of a Scott® paper towel was soaked in the treating solution for 1 minute, and hung in a fume hood for ten minutes to allow the liquid to drip. The wet towels were then transferred to an oven with a set temperature of 95° C. The towels were kept in the oven for approximately one hour and were washed with deionized water three times, followed by drying in air for 24 hours. The add-on level was 4.3%.

150 milligrams of the treated paper towel was tested for odor reduction as described above using 1 microliter of ethyl mercaptan. It was determined that the paper towel had an odor reduction of 68.1%.

Example 11

The effectiveness of the odor control composition of the present invention to adsorb odorous compounds was demonstrated. A treating solution was prepared by dissolving 1.8 grams of PEI (Lupasol WF from BASF, MW=25,000 Daltons) and 1.08 grams of $CuCl_2$ in 300 milliliters of water, followed by adding 1.0 milliliter of a crosslinking agent (Lupasol SC-86X from BASF). A piece of a Scott® paper towel was soaked in the treating solution for 1 minute, and hung in a fume hood for ten minutes to allow the liquid to drip. The wet towels were then transferred to an oven with a set temperature of 95° C. The towels were kept in the oven for approximately one hour and were washed with deionized water three times, followed by drying in the air for 24 hours. The add-on level was 4.2%.

150 milligrams of the treated paper towel was tested for odor reduction as described above using 1 microliter of ethyl mercaptan. It was determined that the paper towel had an odor reduction of 78.8%.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for reducing odor, said method comprising:
    forming a coordination complex between a transition metal and a polydentate compound wherein said polydentate compound is a polyalkylimine;
    crosslinking said polydentate compound, wherein said crosslinking renders said polydentate compound substantially water-insoluble; and
    contacting said coordination complex with an odorous compound so that the one or more active sites of the transition metal capture the odorous compound.

2. A method as defined in claim 1, wherein said transition metal is selected from the group consisting of scandium, titanium, vanadium, chromium, manganese, iron, cobalt, nickel, copper, zinc, silver, gold, and combinations thereof.

3. A method as defined in claim 1, wherein said polydentate compound contains positively charged ligands.

4. A method as defined in claim 1, wherein said polydentate compound contains one or more primary amines, secondary amines, tertiary amines, or combinations thereof.

5. A method as defined in claim 1, wherein said polydentate compound is polyethyleneimine, polypropyleneimine, or a dendrimer thereof.

6. A method as defined in claim 1, wherein a crosslinking agent facilitates said crosslinking of said polydentate compound.

7. A method as defined in claim 6, wherein said crosslinking agent is selected from the group consisting of polyhydric alcohols, polyaziridines, epoxies, haloepoxies, polyaldehydes, polyisocyanates, and combinations thereof.

8. A method as defined in claim 7, wherein said crosslinking agent is an epoxy that contains at least two epoxide groups.

9. A method as defined in claim 7, wherein said crosslinking agent is epichlorohydrin.

10. A method as defined in claim 1, further comprising combining high-surface area particles with said transition metal and said polydentate compound, said particles acting as a carrier for said coordination complex.

11. A method as defined in claim 10, wherein said particles are formed from silica, alumina, or combinations thereof.

12. A method as defined in claim 10, wherein said particles have an average size of less than about 100 nanometers and a surface area of from about 50 to about 1000 square meters per gram.

13. A method as defined in claim 10, wherein said particles have a negative zeta potential.

14. A method as defined in claim 1, further comprising applying said coordination complex to a substrate.

15. A method as defined in claim 14, wherein said substrate comprises a nonwoven, woven, or paper web.

16. A method as defined in claim 14, wherein said substrate comprises cellulosic fibers.

17. A method as defined in claim 16, wherein said coordination complex is chemically grafted to one or more molecules present on said substrate.

18. A method as defined in claim 1, wherein said odorous compound is selected from the group consisting of mercaptans, ammonia, amines, sulfides, ketones, carboxylic acids, aldehydes, terpenoids, hexanol, heptanal, pyridine, and combinations thereof.

19. A method for reducing odor, said method comprising:
    forming a coordination complex between a transition metal and a polyalkylimine, said transition metal being selected from the group consisting of scandium, titanium, vanadium, chromium, manganese, iron, cobalt, nickel, copper, zinc, silver, gold, and combinations thereof;
    crosslinking said polyalkylimine, wherein said crosslinking renders said polyalkylimine substantially water-insoluble;
    applying said coordination complex to a substrate that comprises cellulosic fibers; and
    contacting said substrate with an odorous compound so that the one or more active sites of the transition metal capture the odorous compound.

20. A method as defined in claim 19, wherein said polyalkylimine is polyethyleneimine, polypropyleneimine, or a dendrimer thereof.

21. A method as defined in claim 19, wherein said coordination complex is chemically grafted to one or more molecules present on said cellulosic fibers.

22. A method as defined in claim 19, further comprising combining high-surface area particles with said transition metal and said polyalkylimine, said particles acting as a carrier for said coordination complex.

23. A method as defined in claim 22, wherein said particles are formed from silica, alumina, or combinations thereof.

24. A method as defined in claim 22, wherein said particles have an average size of less than about 100 nanometers and a surface area of from about 50 to about 1000 square meters per gram.

25. A method as defined in claim 19, wherein said odorous compound is selected from the group consisting of mercaptans, ammonia, amines, sulfides, ketones, carboxylic acids, aldehydes, terpenoids, hexanol, heptanal, pyridine, and combinations thereof.

26. A method as defined in claim 19, wherein said polyalkylimine contains positively charged ligands.

* * * * *

UNITED STATES PATENT AND TRADEMARK OFFICE
CERTIFICATE OF CORRECTION

PATENT NO. : 7,754,197 B2  Page 1 of 1
APPLICATION NO. : 10/686937
DATED : July 13, 2010
INVENTOR(S) : Bin Wu et al.

It is certified that error appears in the above-identified patent and that said Letters Patent is hereby corrected as shown below:

Title Page Item 75 the inventor shown as "Bao Trong Kim" should read --Bao Trong Do--.

Signed and Sealed this

Fifth Day of October, 2010

David J. Kappos
*Director of the United States Patent and Trademark Office*